United States Patent [19]

Bird

[11] Patent Number: 4,996,389
[45] Date of Patent: Feb. 26, 1991

[54] ALGAL STRAIN FOR AGAR PRODUCTION
[75] Inventor: Kimon T. Bird, Vero Beach, Fla.
[73] Assignee: Harbor Branch Oceanographic Institution, Inc., Ft. Pierce, Fla.
[21] Appl. No.: 226,814
[22] Filed: Aug. 1, 1988
[51] Int. Cl.$^5$ .................... A01H 13/00; A01G 33/00
[52] U.S. Cl. .................................... 800/200; 800/230; 800/DIG. 7; 435/946; 47/1.4
[58] Field of Search ............................ 47/1.4; 435/946; 800/200, 230, DIG. 7

[56] References Cited

PUBLICATIONS

Craigie et al., (1984) Can. J. Bot. 62 (8): 1665–1670, Abstract, Jan. 1985.
Myers et al., (1980), Plant Physiology 66: 1144–1149.
El Rue, (1984) Allelopathy, Second Edition, Academic Press, Inc., N.Y., pp. 202–204.
Ballantine, D. L., (1979) Bot. Mar. 22(2): 107–110, abstract cited.
Whyte et al., (1980) Bot. Mar. 23(5):277–284, abstract cited.
Van der Meer et al., (1977) Phycologia 16(2): 159–161, abstract cited.
Cheney, D. P., (1984) In Colwell et al., eds., Marine Biotechnology, John Wiley and Sons, N.Y., pp. 161–175.

*Primary Examiner*—Elizabeth C. Weimar
*Assistant Examiner*—Che S. Chereskin
*Attorney, Agent, or Firm*—Carroll F. Palmer

[57] ABSTRACT

A somaclonal variant of *Gracilaria verrucosa*, labeled G-16S, capable of asexual reproduction, has been created which, compared to its parental strain G-16, is less epiphytized, is appreciably less pigmented, and produces agar with substantially enhanced gel strength. This superior algal strain may be used to reduce the relative cost of seaweed cultivation and to produce improved quality agar.

1 Claim, 2 Drawing Sheets

ALGAL STRAIN FOR AGAR PRODUCTION

NOTICE UNDER 35 USC 202(c)(6)

The invention disclosed and claimed herein was made with support from the National Science Foundation and the United States Government has certain rights therein.

FIELD OF THE INVENTION

This application relates to a new strain of seaweed. More particularly it concerns a somaclonal variant of *Gracilaria verrucosa* exhibiting superior properties for agar production.

BACKGROUND OF THE INVENTION

The seaweed *Gracilaria* sp. serves as a source material for the commercial production of agar with strain G-16 being typical of algae commercially cultivated as source material for agar production.

Several needs exist in the commercial cultivation of G-16 and other algae in order to improve such operations and the output of agar in the processing of such source material, e.g., reduction in problems with epiphytes, and increase in gel strength of agar produced from seaweed. Epiphyte control, which can be equated to weeds in farming, is important since this a major cost factor in seaweed farming.

The present invention addresses these needs and provides solutions thereto.

Mutants of various algae occur from time to time and are recognized by those skilled in the art. For example, a mutant of the G-16 strain of *Gracilaria verrucosa* has bee reported in *Phycology Supplement*, Vol.21, page 13, item 56, which had no commercial advantage or useage. The present invention concerns another mutant of G-16 that possesses novel properties rendering it of commercial value and use.

OBJECTS

A principal object of the invention is the provision of a superior algal strain for use in the manufacture of agar.
Other objects are the provision of:
1. A new strain of seaweed that can reduce the cost of seaweed farming per unit quantity of harvested crop.
2. An algal strain that reduces problems with epiphytes in seaweed cultivation.
3. A new agal strain from which agar having increased gel strength as compared with prior known related algal strains.

Other objects and further scope of applicability of the present invention will become apparent from the detailed descriptions given herein; it should be understood, however, that the detailed descriptions, while indicating preferred embodiment of the invention, are given by way of illustration only, since various changes and modifications within the spirit and scope of the invention will become apparent from such descriptions.

SUMMARY OF THE INVENTION

These objects are accomplished according to the invention by the provision of a new somaclonal variant of *Gracilaria verrucosa*, labled G-16S, capable of asexual reproduction, which, as compared to the prior art strain G-16, is less epiphytized, is appreciably less pigmented, and produces agar with appreciably higher gel strength.

The novel somaclonal variant G-16S of the invention exhibits a spectral scan of phycoerythrin (extracted from 1 gm. of biomass and in phosphate buffer) having all peak heights below 0.75 absorbance and with peaks at wavelengths of 565.0, 551.0, 535.6, 534.8, 496.6, 436.4, 428.6, 415.2 and 403.0 nm.

BRIEF DESCRIPTION OF THE DRAWINGS

A more complete understanding of the invention can be obtained by reference to the attached drawings in which.

DESCRIPTION OF THE PREFERRED EMBODIMENTS

A quantity of commercially available *Gracilaria verrucosa* alga G-16 was cultivated under atypical conditions, i.e., 24° C. and low (17 ppt) salinity. These cultivation conditions created a somaclonal variant which was rendered apparent because of its markedly lighter pigmentation and the enhanced gel strength of agar producable therefrom as compared to its parental strain. This new strain has been labeled G-16S and a voucher specimen has been deposited under accession number ATCC40472, deposit date 07/12/88, at The American Type Culture Collection, 12301 Parklawn Drive, Rockville, Maryland 20852.

Figure 2:
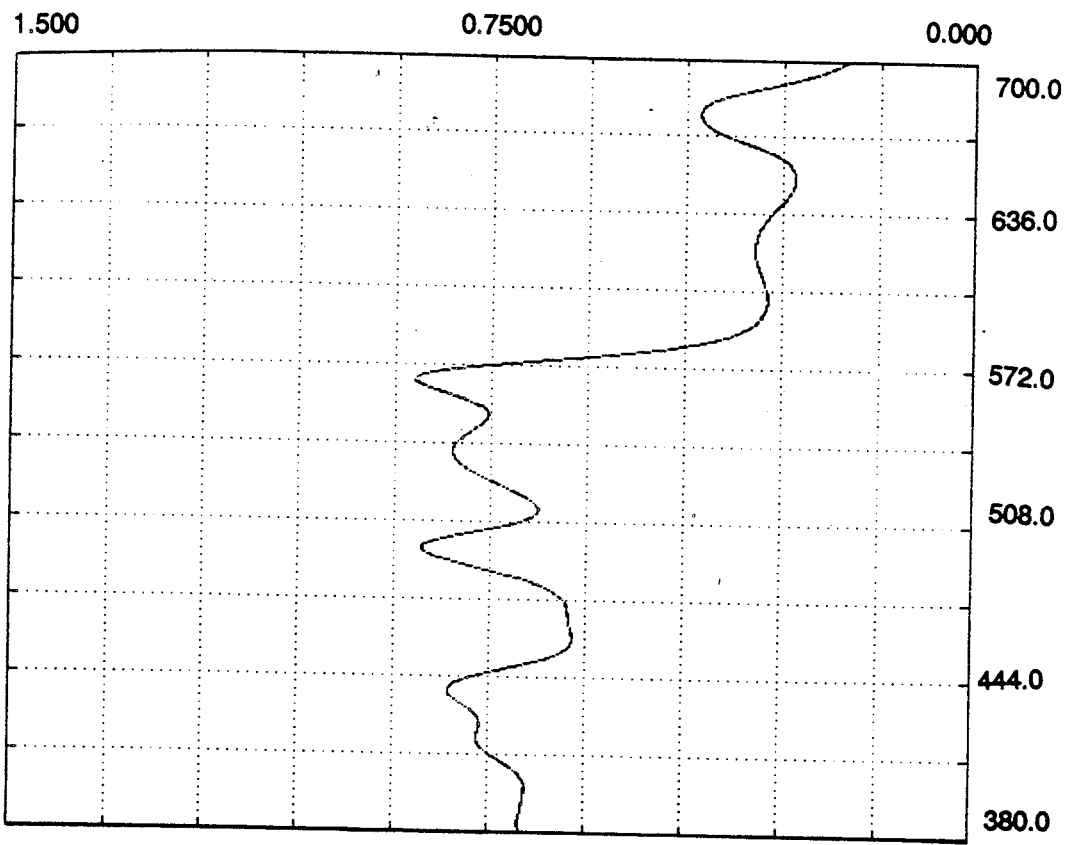
FIG. 2 is a spectrophotometric graph of the light absorbancy of prior art strain of *Gracilaria verrucosa* alga G-16.
Figure 3:
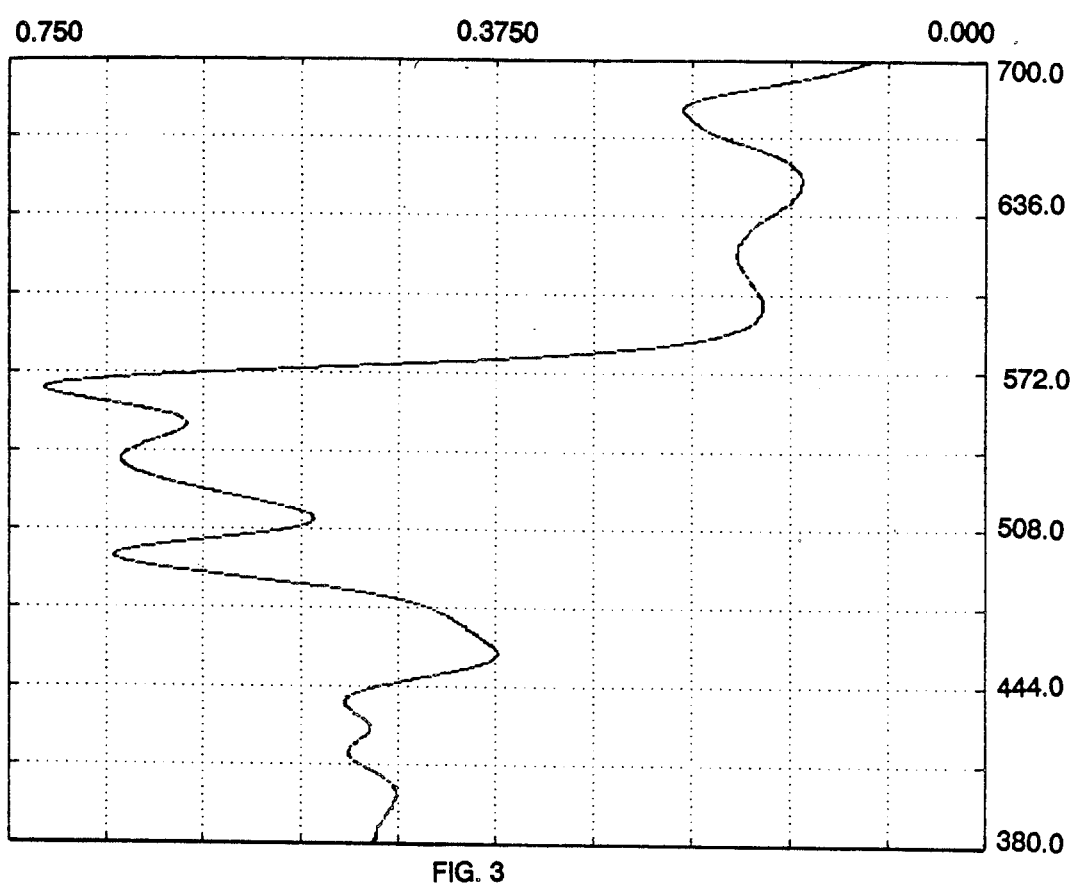
FIG. 3 is a spectrophotometric qraph of the light absorbancy of the new strain of *Gracilaria verrucosa* alga G-16S.

Further evidence that the new strain G-16S is genetically different from G-16, is the spectral differences between G-16S as reported above and G-16 which exhibits an absorbance of 0.87 at a peak height at 566nm and different maxima as shown by a comparison of FIG. 2 with FIG. 3.

A series of cultivations of the prior art alga G-16 and the new alga G-16S under varying conditions were performed, agars were produced from the harvested algal crops using conventional techniques and evaluations were made on the resulting agars. These operations and resulting data are reported below. Example 1.

Creation of the novel strain G-16S was performed by growing cultures of G-16 under different environment conditions/stresses. These conditions included two different light quanta fluxes of 465 and 250 microeinsteins/m$^2$/sec at temperatures of 32, 24 & 15° C. with nitrogen starvation, with nitrogen fertilizers and in salinities of 33 and 17 ppt. The novel strain occurred in a culture grown at 24° C., 17 ppt, 465uE/m$^2$/sec, and with nitrogen fertilizers. It was immediately recognized as a new variety based on its markedly lighter color.
Example 2

Figure 1:
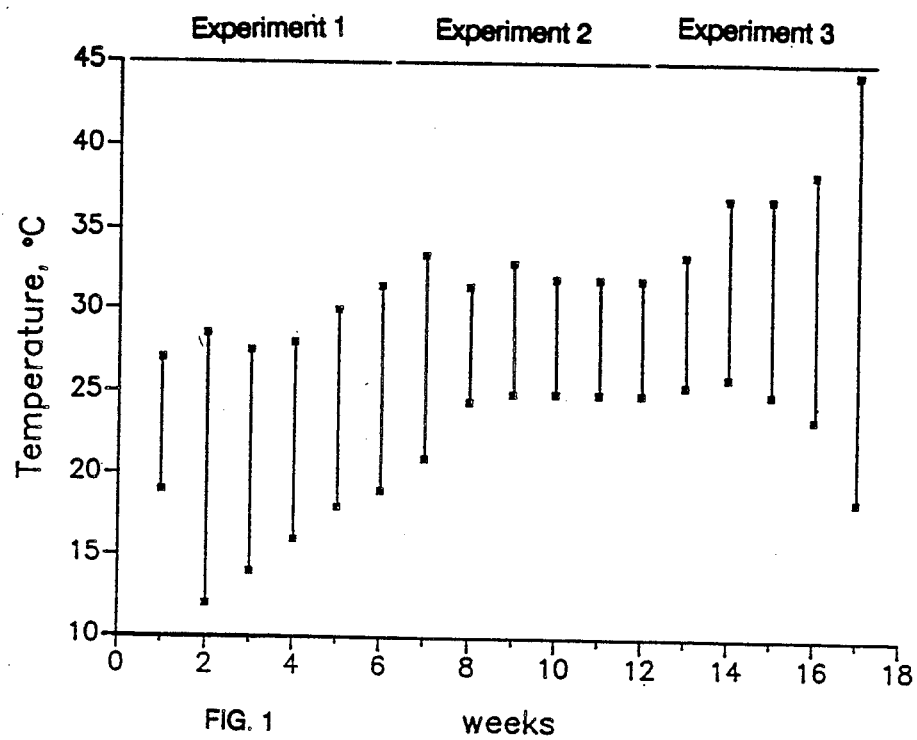
FIG. 1 is a bar graph of temperature variations during the growth of G-16 and G-16S strains to compare agar gel strength over a range of environmental conditions.

Pairs of marine cultivation plots of substantially equal area (0.18 sq.m.) were seeded with *Gracilaria verrucosa* strains G-16 and G-16S and cultivated for periods of six weeks under the temperature conditions shown in FIG. 1. Two different salinity values of the aqueous media in the plots were used, namely, 25 and 33 parts per thousand. The algae grown on the plots were harvested, agar was produced from each separate crop and the resulting agars were tested for gel strength. The agar gel strength data, measured in g/sq.cm., obtained from these operations are reported in the following table:

TABLE I

Cultivations at 33 ppt salinity
Experiment 1 - Low medium cultivation temperatures

|  | G-16 | G-16S |
|---|---|---|
| agar gel strength | 509 | 583 |

Experiment 2 - Moderate median cultivation temperatures

|  | G-16 | G-16S |
|---|---|---|
| agar gel strength | 1048 | 1153 |

Experiment 3 - High medium cultivation temperatures

|  | G-16 | G-16S |
|---|---|---|
| agar gel strength | 603 | 960 |

Cultivations at 25 ppt salinity
Experiment 1 - Low medium cultivation temperatures

|  | G-16 | G-16S |
|---|---|---|
| agar gel strength | 589 | 828 |

TABLE I-continued

Experiment 2 - Moderate median cultivation temperatures

|  | G-16 | G-16S |
|---|---|---|
| agar gel strength | 1074 | 1448 |

Experiment 3 - High medium cultivation temperatures

|  | G-16 | G-16S |
|---|---|---|
| agar gel strength | 650 | 681 |

Ten random grab samples were taken from outdoor cultures of strains G-16 and G-16S grown in similar manner and side by side. The individual samples were weighed. Then epiphytes were separated from each sample and weighted. The strain G-16 samples were found to contain an average of 11±4% epiphytes while the G-16S samples contained 5±3% by weight.

The embodiments of the invention in which an exclusive property of privilege is claimed are:

1. The biologically pure somaclonal variant designated G-16S of the species *Gracilaria verrucosa*.

* * * * *